(12) United States Patent
Avril et al.

(10) Patent No.: US 8,389,779 B2
(45) Date of Patent: Mar. 5, 2013

(54) PROCESS FOR THE PREPARATION OF FLUORINATED COMPOUNDS

(75) Inventors: Karine Avril, Lyons (FR); Bertrand Collier, Saint-Genis-Laval (FR)

(73) Assignee: Arkema France, Colombes (FR)

( * ) Notice: Subject to any disclaimer, the term of this patent is extended or adjusted under 35 U.S.C. 154(b) by 60 days.

(21) Appl. No.: 12/842,737

(22) Filed: Jul. 23, 2010

(65) Prior Publication Data

US 2011/0021849 A1    Jan. 27, 2011

(30) Foreign Application Priority Data

Jul. 23, 2009   (FR) ..................... 09 55139

(51) Int. Cl.
*C07C 17/25* (2006.01)
(52) U.S. Cl. ...................... 570/157; 570/156
(58) Field of Classification Search .............. None
See application file for complete search history.

(56) References Cited

U.S. PATENT DOCUMENTS

| | | | |
|---|---|---|---|
| 2007/0100175 A1* | 5/2007 | Miller et al. | ................. 570/178 |
| 2007/0179324 A1 | 8/2007 | Van Der Puy et al. | |

FOREIGN PATENT DOCUMENTS

| | | |
|---|---|---|
| EP | 0644173 A1 | 3/1995 |
| WO | WO 2007056194 | 5/2007 |
| WO | WO 2008002499 | 1/2008 |
| WO | WO 2008002500 | 1/2008 |
| WO | WO 2008030440 A2 | 3/2008 |
| WO | WO 2008075017 | 6/2008 |
| WO | WO 2009084703 A1 | 7/2009 |
| WO | WO 2009138764 | 11/2009 |

OTHER PUBLICATIONS

Knunyants, et al; Communication 13. "*Catalytic Hydrogenation of Perfluoro Olefins*" Institute of Heteroorganic Compounds, Academy of Sciences of the USR Translated from Izvestiya Akademii Nauk SSSR, Otdelenie Khimicheskikh Nauk, No. 8, pp. 1412-1418, Aug. 1960; Original Article submitted Mar. 3, 1959.

* cited by examiner

*Primary Examiner* — Sudhakar Katakam
(74) *Attorney, Agent, or Firm* — Hunton & Williams, LLP

(57) ABSTRACT

A subject-matter of the invention is a process for the preparation of 2,3,3,3-tetrafluoro-1-propene comprising the following stages: (i) hydrogenation of hexafluoropropylene to give 1,1,1,2,3,3-hexafluoropropane; (ii) dehydrofluorination of the 1,1,1,2,3,3-hexafluoropropane obtained in the preceding stage to give 1,2,3,3,3-pentafluoro-1-propene; (iii) hydrogenation of the 1,2,3,3,3-pentafluoro-1-propene obtained in the preceding stage to give 1,1,1,2,3-pentafluoropropane; (iv) purification of the 1,1,1,2,3-pentafluoropropane obtained in the preceding stage; and (v) dehydrofluorination of the 1,1,1,2,3-pentafluoropropane obtained in the preceding stage to give 2,3,3,3-tetrafluoro-1-propene; and (vi) purification of the 2,3,3,3-tetrafluoro-1-propene of the preceding stage.

18 Claims, 1 Drawing Sheet

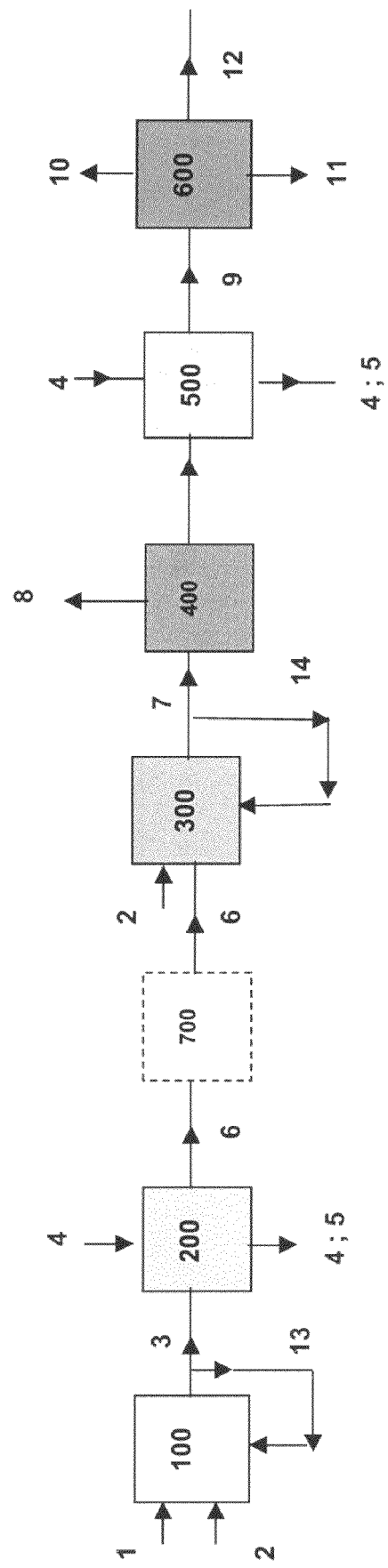

PROCESS FOR THE PREPARATION OF FLUORINATED COMPOUNDS

CROSS-REFERENCE TO RELATED APPLICATIONS

This application claims the benefit of French Application No. FR 09.55139, filed Jul. 23, 2009, the disclosure of which is incorporated herein by reference in its entirety.

BACKGROUND

A subject-matter of the invention is a process for the preparation of fluorinated compounds, namely the fluorinated compound 2,3,3,3-tetrafluoro-1-propene.

Hydrofluorocarbons (HFCs) and in particular hydrofluoroolefins, such as 2,3,3,3-tetrafluoro-1-propene (HFO-1234yf), are compounds known for their properties of refrigerants and heat-transfer fluids, extinguishers, propellants, foaming agents, blowing agents, gaseous dielectrics, monomer or polymerization medium, support fluids, agents for abrasives, drying agents and fluids for energy production units. Unlike CFCs and HCFCs, which are potentially dangerous to the ozone layer, HFOs do not comprise chlorine and thus do not present a problem for the ozone layer.

Several processes for the manufacture of 1234yf are known.

WO2008/002499 describes a process for the production of a mixture of 2,3,3,3-tetrafluoro-1-propene (HFO-1234yf) and 1,3,3,3-tetrafluoro-1-propene (HFO-1234ze) by pyrolysis of 1,1,1,2,3-pentafluoropropane (HFC-245eb).

WO2008/002500 describes a process for production of a mixture of 2,3,3,3-tetrafluoro-1-propene (HFO-1234yf) and 1,3,3,3-tetrafluoro-1-propene (HFO-1234ze) by catalytic conversion of 1,1,1,2,3-pentafluoropropane (HFC-245eb) over a dehydrofluorination catalyst.

These two abovementioned patent applications are thus targeted at the production of a mixture comprising a substantial portion of product HFO-1234ze.

WO2007/056194 describes the preparation of HFO-1234yf by dehydrofluorination of HFC-245eb either with potassium hydroxide, typically an aqueous solution of at most 50% by weight of KOH, or in the gas phase in the presence of a catalyst, in particular a catalyst based on nickel, carbon or a combination of these.

The document Knunyants et al., Journal of the USSR Academy of Sciences, Chemistry Department, "Reactions of fluoro-olefins", Report 13, "Catalytic hydrogenation of perfluoro-olefins", 1960, clearly describes various chemical reactions on fluorinated compounds. This document describes the substantially quantitative hydrogenation of HFP over a catalyst based on palladium supported on alumina, the temperature changing from 20° C. to 50° C. and then being maintained at this value. This document describes the dehydrofluorination of 1,1,1,2,3,3-hexafluoropropane (HFC-236ea) by passing through a suspension of KOH in dibutyl ether, in order to produce 1,2,3,3,3-pentafluoro-1-propene (HFO-1225ye) with a yield of only 60%. This document describes the hydrogenation of 1,2,3,3,3-pentafluoro-1-propene (HFO-1225ye) to give 1,1,1,2,3-pentafluoropropane (HFC-245eb) over a catalyst formed of palladium supported on alumina. During this hydrogenation, a hydrogenolysis reaction also takes place, a significant amount of 1,1,1,2-tetrafluoropropane being produced. This document describes the dehydrofluorination of 1,1,1,2,3-pentafluoropropane (HFC-245eb) to give 2,3,3,3-tetrafluoro-1-propene (HFO-1234yf) by passing into a suspension of KOH powder in dibutyl ether, with a yield of only 70%. These reactions are described independently of one another, although it is indicated that it is possible to combine them in order to synthesize a range of ethylene, propylene and isobutylene derivatives comprising variable amounts of fluorine.

The document U.S. Pat. No. 5,396,000 describes the preparation of 1,1,1,2,3-pentafluoropropane by catalytic dehydrofluorination of 1,1,1,2,3,3-hexafluoropropane (HFC-236ea) to give 1,2,3,3,3-pentafluoro-1-propene (HFO-1225ye), followed by a hydrogenation in order to produce the desired compound. The dehydrohalogenation of HFC-236ea to give HFO-1225ye is carried out in the gas phase, the reaction product being, in one example, conveyed directly to the following reactor in which the hydrogenation of the compound HFO-1225ye to give the compound HFC-245eb takes place. It is also indicated in this document that the compound HFC-236ea can be obtained by hydrogenation of hexafluoropropylene (HFP).

The document U.S. Pat. No. 5,679,875 describes the preparation of 1,1,1,2,3-pentafluoropropane by catalytic dehydrofluorination of 1,1,1,2,3,3-hexafluoropropane (HFC-236ea) to give 1,2,3,3,3-pentafluoro-1-propene (HFO-1225ye), followed by hydrogenation to produce the desired compound. The reactions are carried out in the gas phase. It is also indicated in this document that the compound HFC-236ea can be obtained by hydrogenation of hexafluoropropylene (HFP).

The document WO 2008/030440 describes the preparation of HFO-1234yf from HFO-1225ye by reacting HFO-1225ye with hydrogen in the presence of a catalyst, in order to give HFC-245eb, and by then reacting the HFC-245eb with a basic aqueous solution in the presence of a phase transfer catalyst and a non-aqueous and non-alcoholic solvent.

The document WO 2008/075017 illustrates the dehydrofluorination reaction of 1,1,1,2,3,3-hexafluoropropane (HFC-236ea) to give 1,1,1,2,3-pentafluoropropene (HFO-1225ye) at 150° C. in the presence of a 50% by weight aqueous KOH solution. In the absence of a phase transfer catalyst, the conversion after 3 and a half hours is 57.8% and the selectivity for HFO-1225ye is 52.4% (Test 1). In the presence of a phase transfer catalyst, this conversion is achieved after only 2.5 hours and the selectivity is virtually unchanged (Test 4). As indicated in Table 2 of this document, it is necessary to use an organic solvent in order to increase the selectivity for HFO-1225ye.

There exists a need for a process for the preparation of high-purity HFO-1234yf from a starting material which is easily accessible and which results in the desired product with a high selectivity, preferably a high yield and advantageously a high productive output.

The Applicant Company has noticed that some by-products generated in the various stages of process for the manufacture of HFO-1234yf, in particular those having a boiling point in the vicinity of that of HFO-1234yf, separate with difficulty from HFO-1234yf and require very strict conditions which are generally expensive.

Likewise, some unreacted reactants in the various stages or intermediate products in the process are difficult to separate from HFO-1234yf. Mention may be made, by way of example, of HFP.

SUMMARY OF THE INVENTION

The present invention thus provides a process for the manufacture of high-purity HFO-1234yf which does not exhibit the abovementioned disadvantages.

The process for the preparation of 2,3,3,3-tetrafluoro-1-propene according to the present invention comprises the following stages:
  (i) gas-phase hydrogenation of hexafluoro-propylene to give 1,1,1,2,3,3-hexafluoro-propane in the presence of a super-stoichiometric amount of hydrogen and of a catalyst in a reactor;
  (ii) dehydrofluorination of the 1,1,1,2,3,3-hexa-fluoropropane obtained in the preceding stage to give 1,2,3,3,3-pentafluoro-1-propene in the presence of a dehydrofluorination catalyst or using a water and potassium hydroxide mixture;
  (iii) gas-phase hydrogenation of the 1,2,3,3,3-pentafluoro-1-propene obtained in the preceding stage to give 1,1,1,2,3-penta-fluoropropane in the presence of a superstoichiometric amount of hydrogen and of a catalyst in a reactor;
  (iv) purification of the 1,1,1,2,3-pentafluoro-propane obtained in the preceding stage;
  (v) dehydrofluorination of the purified 1,1,1,2,3-pentafluoropropane to give 2,3,3,3-tetrafluoro-1-propene in the presence of a dehydrofluorination catalyst or using a water and potassium hydroxide mixture;
  (vi) purification of the 2,3,3,3-tetrafluoro-1-propene obtained in the preceding stage.

The process according to the present invention can additionally comprise at least one of the following characteristics:
  the hydrogenation stage(s) (i) and/or (iii) is (are) carried out in a single- or multistage adiabatic reactor or in at least two adiabatic reactors in series;
  a portion of the gaseous output stream resulting from the hydrogenation stage (i) comprising HFC-236ea and unreacted hydrogen is recycled to the stage (i);
  the gaseous output stream resulting from the hydrogenation stage (i) is subjected to a condensation stage under conditions such that the unreacted hydrogen is not condensed and that a portion of the HFC-236ea formed in stage (i) is condensed;
  a portion of the gaseous output stream resulting from the hydrogenation stage (iii) comprising HFC-245eb and unreacted hydrogen is recycled to stage (iii);
  the gaseous output stream resulting from the hydrogenation stage (iii) is subjected to a condensation stage under conditions such that the unreacted hydrogen is not condensed and that a portion of the HFC-245eb formed in stage (i) is condensed;
  the potassium hydroxide is present in the reaction medium of stage (ii) and/or (v) in an amount of between 20 and 75% by weight and advantageously of between 55 and 70% by weight, with respect to the weight of the water and KOH mixture;
  a stage of treatment of the potassium fluoride, coproduced in the dehydrofluorination stage (ii) and/or (v), with calcium hydroxide;
  a stage of purification of the 1,2,3,3,3-penta-fluoro-1-propene obtained in the dehydro-fluorination stage (ii).

FIG. 1 is a schematic illustration of a preferred embodiment of the invention.

DETAILED DESCRIPTION OF PREFERRED EMBODIMENTS

The purity of the 2,3,3,3-tetrafluoro-1-propene obtained according to the present invention is preferably greater than 99.5% by weight and advantageously greater than 99.8% by weight.

The aim of the purification stage (iv) is to purify the stream comprising HFC-245eb originating from the hydrogenation stage (iii) for the purpose of obtaining HFC-245eb, with a purity preferably of greater than 98% by weight, intended for the dehydrofluorination stage (v).

This purification stage preferably consists in removing compounds which have a similar boiling point (plus or minus 10° C.) to that of HFO-1234yf or in removing precursors of the said compounds having a boiling point lower by at least 20° C., and even lower by at least 10° C., with respect to that of HFC-245eb.

The compounds to be removed in the purification stage (iv) are preferably chosen from hexafluoropropene, cyclohexafluoropropene, 1,2,3,3,3-pentafluoropropene (Z and E isomers), 1,1,3,3,3-pentafluoropropene (HFO-1225zc), 1,1,1,2-tetrafluoropropane (HFC-254eb), 3,3,3-trifluoropropene (HFO-1243zf), 1,1,1,2-tetrafluoroethane (HFC-134a), 1,1,2-trifluoroethane (HFC-143) and 1,1,1,2,3,3-hexafluoropropane.

The compounds to be removed in the purification stage (iv) are advantageously chosen from 1,2,3,3,3-penta-fluoropropene (Z and E isomers), 1,1,3,3,3-pentafluoropropene (HFO-1225zc) and 1,1,1,2-tetrafluoroethane (HFC-134a).

The process according to the present invention can be carried out batchwise, semicontinuously or continuously. Preferably, the process according to the present invention is carried out continuously and the stream originating from the preceding stage is conveyed directly to the following stage, after optional purification. An economical process for the preparation of the compound HFO-1234yf of high purity is thus obtained, the starting material, HFP, being readily available commercially at a low cost.

Hydrogenation Stage (i)

The hydrogenation stage can be carried out in the presence of an $H_2$/HFP molar ratio of between 1.1 and 40, preferably between 2 and 15.

The hydrogenation stage can be carried out at a pressure of between 0.5 and 20 bar absolute and preferably between 1 and 5 bar absolute.

Mention may in particular be made, as catalysts capable of being used in the hydrogenation stage, of catalysts based on a metal from Group VIII or rhenium which is optionally supported, for example on carbon, silicon carbide, alumina or aluminium fluoride.

Use may be made, as metal, of platinum or palladium, in particular palladium, advantageously supported on carbon or alumina. It is also possible to combine this metal with another metal, such as silver, copper, gold, tellurium, zinc, chromium, molybdenum and thallium.

The catalyst can be present in any appropriate form, extrudates, pellets or beads.

Preferably, use is made of a catalyst comprising between 0.05 and 10% by weight and advantageously between 0.1 and 5% by weight of palladium supported on alumina or carbon.

The hydrogenation stage can be carried out under conditions such that the temperature at the inlet of the reactor is between 30 and 200° C., preferably between 30 and 100° C., and the temperature at the outlet of the reactor is between 50 and 250° C., preferably between 80 and 150° C.

The contact time (ratio of the volume of catalyst to the total gas stream under standard temperature and pressure conditions) is preferably between 0.2 and 10 seconds and advantageously between 1 and 5 seconds.

This hydrogenation stage can be carried out in an optionally multistage adiabatic reactor or in at least two adiabatic reactors in series.

The stage of hydrogenation of HFP is substantially quantitative.

Preferably, a portion of the gaseous output stream resulting from the hydrogenation stage (i) comprising HFC-236ea and unreacted hydrogen is recycled to stage (i).

Advantageously, the gaseous output stream resulting from the hydrogenation stage (i) is subjected to a condensation stage under conditions such that the unreacted hydrogen is not condensed and that a portion of the HFC-236ea formed in stage (i) is condensed.

Preferably, the condensation stage is carried out at a temperature of between 0 and 50° C. and at a pressure of between 0.5 and 20 bar absolute, advantageously between 1 and 5 bar absolute.

Preferably, the condensation stage is carried out under conditions such that between 1 and 30% of the HFC-236ea at the outlet of stage (i) is condensed and advantageously between 2 and 10% is condensed.

The noncondensed fraction is subsequently recycled to the hydrogenation stage (i) after optionally being heated.

Dehydrofluorination Stage (ii)

The HFC-236ea formed in stage (1), after optional condensation and evaporation, is subsequently subjected to a stage of dehydrofluorination, preferably using potassium hydroxide, advantageously carried out in a stirred reactor. The potassium hydroxide is preferably present in the reaction medium in an amount of between 20 and 75% by weight and advantageously of between 55 and 70% by weight, with respect to the weight of water and KOH mixture.

The aqueous reaction medium of the dehydrofluorination stage comprising KOH is preferably maintained at a temperature of between 80 and 180° C., advantageously of between 125 and 180° C. A particularly preferred temperature of the reaction medium is between 145 and 165° C.

The stage of dehydrofluorination using KOH can be carried out at a pressure of 0.5 to 20 bar but it is preferable to operate at a pressure of between 0.5 and 5 bar absolute and more advantageously between 1.1 and 2.5 bar absolute.

Potassium fluoride is formed during the stage of dehydrofluorination using KOH.

The process according to the present invention can comprise a treatment stage during which the potassium fluoride coproduced in the dehydrofluorination stage is brought into contact with calcium hydroxide in an aqueous reaction medium at a temperature preferably of between 50 and 150° C., advantageously of between 70 and 120° C. and more advantageously between 70 and 100° C.

This treatment stage is preferably carried out by introducing calcium hydroxide into a reactor comprising a portion of the reaction medium originating from the dehydrofluorination stage comprising potassium fluoride, potassium hydroxide and water, after optional dilution.

The potassium fluoride is preferably present at between 4 and 45% by weight and advantageously between 7 and 20% by weight, with respect to the reaction medium originating from the dehydrofluorination stage.

The reaction medium of the treatment preferably comprises between 4 and 50% by weight of potassium hydroxide and advantageously between 10 and 35% by weight of potassium hydroxide, with respect to the total weight of potassium hydroxide and water in the medium.

The stage of treatment with calcium hydroxide makes it possible to regenerate potassium hydroxide, which can be recycled to the dehydrofluorination stage, and to obtain calcium fluoride of commercial quality which can be recovered in value after separation, for example by filtration and settling.

Calcium fluoride with a mean size of between 20 and 35 µm (mean size at 50% by weight of the particle size distribution) is obtained under the preferred conditions of this treatment stage.

The stage of treatment with calcium hydroxide can be carried out in any type of reactor known to a person skilled in the art, for example a stirred reactor.

Hydrogenation Stage (iii)

The HFO-1225ye obtained in stage (ii), optionally after purification, is subjected to a stage of hydrogenation in the presence of a catalyst.

The purification of the HFO-1225ye can comprise a double distillation with removal of the light impurities in the first distillation and removal of the heavy impurities in the second distillation.

The hydrogenation stage can be carried out in the presence of an $H_2$/HFO-1225ye molar ratio of between 1.1 and 40, preferably between 2 and 15.

The hydrogenation stage can be carried out at a pressure of between 0.5 and 20 bar absolute and preferably between 1 and 5 bar absolute.

Mention may in particular be made, as catalysts capable of being used in the hydrogenation stage, of catalysts based on a metal from Group VIII or rhenium which is optionally supported, for example on carbon, silicon carbide, alumina or aluminium fluoride.

Use may be made, as metal, of platinum or palladium, in particular palladium, advantageously supported on carbon or alumina. It is also possible to combine this metal with another metal, such as silver, copper, gold, tellurium, zinc, chromium, molybdenum and thallium.

The catalyst can be present in any appropriate form, extrudates, pellets or beads.

Preferably, use is made of a catalyst comprising between 0.05 and 10% by weight and advantageously between 0.1 and 5% by weight of palladium supported on alumina or carbon.

The hydrogenation stage can be carried out under conditions such that the temperature at the inlet of the reactor is between 50 and 200° C., preferably between 80 and 140° C., and the temperature at the outlet of the reactor is between 80 and 250° C., preferably between 110 and 160° C.

The contact time (ratio of the volume of catalyst to the total gas stream under standard temperature and pressure conditions) is preferably between 0.2 and 10 seconds and advantageously between 1 and 5 seconds.

This hydrogenation stage can be carried out in an optionally multistage adiabatic reactor or in at least two adiabatic reactors in series.

The stage of hydrogenation of the HFO-1225ye is substantially quantitative.

Preferably, a portion of the gaseous output stream resulting from the hydrogenation stage (iii) comprising HFC-245eb and unreacted hydrogen is recycled to stage (iii).

Advantageously, the gaseous output stream resulting from the hydrogenation stage (iii) is subjected to a condensation stage under conditions such that the unreacted hydrogen is not condensed and that a portion of the HFC-245eb formed in stage (iii) is condensed.

Preferably, the condensation stage is carried out at a temperature of between 0 and 50° C. and at a pressure of between 0.5 and 20 bar absolute, advantageously between 1 and 5 bar absolute.

Preferably, the condensation stage is carried out under conditions such that between 1 and 30% of HFC-245eb at the outlet of stage (iii) is condensed and advantageously between 2 and 10% is condensed.

The noncondensed fraction is subsequently recycled to the hydrogenation stage (iii) after optionally being heated.

Purification Stage (iv)

The HFC-245eb obtained in the hydrogenation stage (iii), after optional condensation, is subjected to a purification stage for the purposes of obtaining HFC-245eb, with a purity of preferably greater than 98% by weight, intended for the dehydrofluorination stage (v).

This purification stage preferably consists in removing compounds which have a boiling point similar to that of HFO-1234yf or precursors of the said compounds having a boiling point lower by at least 20° C., indeed even lower by at least 10° C., with respect to that of HFC-245eb.

These compounds can be by-products from the various stages of the process, unreacted reactants of the various stages and/or intermediates of the process.

This purification stage preferably comprises at least one conventional distillation stage carried out at a pressure of between 1 and 20 bar absolute and advantageously between 5 and 10 bar absolute.

Dehydrofluorination Stage (v)

The HFC-245eb purified in stage (iv), with a purity preferably of greater than 98% by weight, is subsequently subjected to a stage of dehydrofluorination, preferably using potassium hydroxide, advantageously carried out in a stirred reactor. The potassium hydroxide is Preferably present in the reaction medium in an amount of between 20 and 75% by weight and advantageously of between 55 and 70% by weight, with respect to the weight of the water and KOH mixture.

The aqueous reaction medium comprising KOH of the dehydrofluorination stage is preferably maintained at a temperature of between 80 and 180° C., advantageously of between 125 and 180° C. A particularly preferred temperature of the reaction medium is between 145 and 165° C.

The dehydrofluorination stage can be carried out at a pressure of 0.5 to 20 bar but it is preferable to operate at a pressure of between 0.5 and 5 absolute and more advantageously between 1.1 and 2.5 bar absolute.

Potassium fluoride is formed during the stage of dehydrofluorination using KOH.

The process according to the present invention can comprise a treatment stage during which the potassium fluoride coproduced in the dehydrofluorination stage is brought into contact with calcium hydroxide in an aqueous reaction medium at a temperature preferably of between 50 and 150° C., advantageously of between 70 and 120° C. and more advantageously between 70 and 100° C.

This treatment stage is preferably carried out by introducing calcium hydroxide into a reactor comprising a portion of the reaction medium originating from the dehydrofluorination stage comprising potassium fluoride, potassium hydroxide and water, after optional dilution.

The potassium fluoride is preferably present at between 4 and 45% by weight and advantageously between 7 and 20% by weight, with respect to the reaction medium originating from the dehydrofluorination stage.

The reaction medium of the treatment preferably comprises between 4 and 50% by weight of potassium hydroxide and advantageously between 10 and 35% by weight of potassium hydroxide, with respect to the total weight of potassium hydroxide and water in the medium.

The stage of treatment with calcium hydroxide makes it possible to regenerate potassium hydroxide, which can be recycled to the dehydrofluorination stage, and to obtain calcium fluoride of commercial quality which can be recovered in value after separation, for example by filtration and settling.

Calcium fluoride with a mean size of between 20 and 35 μm (mean size at 50% by weight of the particle size distribution) is obtained under the preferred conditions of this treatment stage.

The stage of treatment with calcium hydroxide can be carried out in any type of reactor known to a person skilled in the art, for example a stirred reactor.

Purification Stage (vi)

The gas stream on conclusion of the dehydrofluorination stage (v), comprising the HFO-1234yf, the unreacted HFC-245eb and the by products, is subjected to a purification stage in order to obtain HFO-1234yf having a purity of at least 99.5% by weight, preferably of least 99.8% by weight.

The purification preferably comprises a first distillation stage, in order to separate the light impurities, in particular trifluoropropyne, and a second distillation stage, in order to separate the HFO-1234yf from the heavy impurities, in particular HFC-245eb.

According to a particularly preferred embodiment (FIG. 1) of the invention, (i) hexafluoropropylene (1) is reacted continuously with hydrogen (2) in the gas phase in a superstoichiometric amount, in an adiabatic reactor (100), in the presence of a catalyst, to give 1,1,1,2,3,3-hexafluoropropane, and a portion (13) of the gaseous output stream resulting from this reaction is recycled; (ii) the nonrecycled part (3) of the output stream resulting from stage (i), comprising 1,1,1,2,3,3-hexafluoropropane, is reacted with potassium hydroxide (4) present in an aqueous reaction medium (200), in an amount of between 20 and 75% by weight and preferably of between 55 and 70% by weight, with respect to the weight of the water and KOH mixture of the reaction medium, maintained at a temperature of between 80 and 180° C., preferably of between 145 and 165° C., to give 1,2,3,3,3-pentafluoro-1-propene and potassium fluoride; (iii) the 1,2,3,3,3-pentafluoro-1-propene (6) obtained in stage (ii) is reacted with hydrogen (2) in the gas phase in a superstoichiometric amount, in an adiabatic reactor (300), in the presence of a catalyst, to give 1,1,1,2,3-penta-fluoropropane and a portion (14) of the gaseous output stream resulting from this reaction is recycled; (iv) the nonrecycled portion (7) of the output stream resulting from stage (iii), comprising 1,1,1,2,3-pentafluoropropane, is subjected to a purification stage (400) in order to remove impurities (8) and thus to obtain 1,1,1,2,3-pentafluoropropane, with a purity preferably of greater than 98% by weight; (v) the 1,1,1,2,3-pentafluoropropane obtained after the purification of stage (iv) is reacted with potassium hydroxide (4) present in an aqueous reaction medium (500), in an amount of between 20 and 75% by weight and preferably of between 55 and 70% by weight, with respect to the weight of the water and KOH mixture of the reaction medium, maintained at a temperature of between 80 and 180° C., preferably of between 145 and 165° C., to give 2,3,3,3-tetrafluoro-1-propene and potassium fluoride; and (vi) the gas stream (9) resulting from the dehydrofluorination stage (v), comprising HFO-1234yf, the unreacted HFC-245eb and the by products, is subjected to a purification stage (600) in order to obtain HFO-1234yf (12) having a purity of greater than 99.5% by weight, preferably of greater than 99.8% by weight. The light by products (10) separated from HFO-1234yf can be subjected to a treatment and the unreacted HFC-245eb (11) can be recycled in (500).

The purification of stage (iv) preferably comprises a conventional distillation at a pressure of between 1 and 20 bar absolute.

The potassium fluoride (5) formed in stage (ii) and stage (v) can be subjected to a treatment with calcium hydroxide under the conditions described above to regenerate the potassium hydroxide and to form calcium fluoride.

The HFO-1225ye obtained in stage (ii) can be subjected to a purification stage (700), preferably to a double distillation, before the hydrogenation reaction of stage (iii).

The gaseous output stream on conclusion of the hydrogenation stage (i) and/or (iii) can be partially condensed; the noncondensed portion, comprising all the unreacted hydrogen, is recycled.

The hydrogenation stages (i) and (iii) can be carried out under the conditions described above.

Experimental Part

A mixture comprising 1 g of hexafluoropropene, 1 g of cyclohexafluoropropene, 1 g of HFO-1234yf, 0.2 g of HFC-134a, 1 g of HFO-1243zf, 0.1 g of HFO-1225zc, 10 g of HFO-1225ye (Z or E), 40 g of HFC-254eb, 0.01 g of HFC-143, 1 g of HFC-236ea 0.5 g of hydrofluoric acid and 944.19 g of HFC-245eb is distilled in a column comprising 40 theoretical plates.

The distillation is carried out at 6 bar absolute, with a column bottom temperature of approximately 80° C. and a top temperature of 50° C.

At the end of the distillation, the column bottoms are analysed and 0.001 g of HFC-143, 0.094 g of HFC-236ea and 938 g of HFC-245eb are found. The other compounds were removed at the column top.

The distilled HFC-245eb is subsequently subjected to a dehydrofluorination stage in the stirred reactor in the presence of a water and potassium hydroxide mixture. The mixture is maintained at 150° C. and the KOH in the mixture represents 65% by weight, with respect to the water/KOH total weight.

The HFO-1234yf formed is condensed and then subjected to a distillation in a column maintained, to begin with, at a pressure of 13 bar and a bottom temperature of 60° C., in order to separate the trifluoropropyne, and subsequently at a pressure of 11 bar and a top temperature of 50° C., in order to obtain, at the top, HFO-1234yf with a purity of greater than 99.9% by weight.

The invention claimed is:

1. A process for the preparation of 2,3,3,3-tetrafluoro-1-propene comprising the following steps:
   (i) hydrogenating hexafluoropropylene in the gas phase in the presence of a super-stoichiometric amount of hydrogen and of a hydrogenation catalyst in a reactor to yield 1,1,1,2,3,3-hexafluoropropane;
   (ii) dehydrofluorinating the 1,1,1,2,3,3-hexafluoropropane obtained in the preceding step in the presence of a dehydrofluorination catalyst or a water and potassium hydroxide mixture to yield 1,2,3,3,3-pentafluoro-1-propene;
   (iii) hydrogenating the 1,2,3,3,3-pentafluoro-1-propene obtained in the preceding step in the gas phase in the presence of a superstoichiometric amount of hydrogen and of a catalyst in a reactor to yield 1,1,1,2,3-pentafluoropropane;
   (iv) purifying the 1,1,1,2,3-pentafluoropropane obtained in the preceding step to a purity greater than 98% by weight;
   (v) dehydrofluorinating the purified 1,1,1,2,3-pentafluoropropane in the presence of a dehydrofluorination catalyst or a water and potassium hydroxide mixture, to yield 2,3,3,3-tetra-fluoro-1-propene;
   (vi) purifying the 2,3,3,3-tetrafluoro-1-propene obtained in the preceding step to yield the 2,3,3,3-tetrafluoro-1-propene in a purity greater than 99.5% by weight.

2. The process of claim 1, wherein the purifying of the 1,1,1,2,3-pentafluoropropane in step (iv) comprises a distillation step at a pressure ranging from 1 to 20 bar absolute.

3. The process of claim 1, wherein the compounds to be removed in step (iv) have a boiling point at least 20° C. lower than the boiling point of 1,1,1,2,3-penta-fluoropropane.

4. The process of claim 3, wherein the compounds to be removed in step (iv) have a boiling point at least 10° C. lower than the boiling point of 1,1,1,2,3-penta-fluoropropane.

5. The process of claim 1, wherein the amount of potassium hydroxide in the water/potassium hydroxide mixtures of steps (ii) and/or (v) ranges from 55 to 75% by weight of the water/potassium hydroxide mixture.

6. The process of claim 1, wherein step (ii) and/or step (v) is or are carried out at a temperature ranging from 80 to 180° C.

7. The process of claim 6, wherein step (ii) and/or step (v) is or are carried out at a temperature ranging from 145 to 165° C.

8. The process of claim 1, wherein a stream resulting from step (ii) is purified before step (iii) is performed.

9. The process of claim 8, wherein the purification comprises a double distillation.

10. The process of claim 1, wherein said process is carried out continuously.

11. Process of claim 1, wherein step (i) and/or step (iii) is or are carried out in an optionally multistep adiabatic reactor or in at least two adiabatic reactors in series.

12. The process of claim 1, wherein a portion of a gaseous output stream resulting from step (i) and/or (iii) is recycled.

13. The process of claim 1, further comprising partially condensing a gaseous output stream resulting from step (i) and/or (iii).

14. The process of claim 1, further comprising treating potassium fluoride coproduced in the dehydrofluorination steps (ii) and (v) with calcium hydroxide.

15. The process of claim 1, wherein the catalyst of step (i) and/or step (iii) comprises from 5 to 10% by weight of palladium supported on alumina or carbon.

16. The process of claim 15, wherein the catalyst of step (i) and/or step (iii) comprises from 0.1 to 5% by weight of palladium supported on alumina or carbon.

17. The process of claim 1, wherein the reactor of step (i) has a temperature at the inlet of the reactor ranging from 30 to 100° C.

18. The process of claim 1, wherein the reactor of step (iii) has a temperature at the inlet of the reactor ranging from 80 to 140° C.

* * * * *